(12) United States Patent
Suh

(10) Patent No.: US 7,500,976 B2
(45) Date of Patent: Mar. 10, 2009

(54) TRANSLATIONAL SCISSOR PLATE FIXATION SYSTEM

(75) Inventor: Sean S Suh, Plymouth Meeting, PA (US)

(73) Assignee: Synthes USA, LLC, West Chester, PA (US)

( * ) Notice: Subject to any disclaimer, the term of this patent is extended or adjusted under 35 U.S.C. 154(b) by 161 days.

(21) Appl. No.: 11/078,799

(22) Filed: Mar. 11, 2005

(65) Prior Publication Data

US 2006/0217723 A1 Sep. 28, 2006

(51) Int. Cl.
*A61B 17/80* (2006.01)
(52) U.S. Cl. .................................................. 606/70
(58) Field of Classification Search .......... 606/69, 606/70, 71
See application file for complete search history.

(56) References Cited

U.S. PATENT DOCUMENTS

| | | | | |
|---|---|---|---|---|
| 5,718,705 | A * | 2/1998 | Sammarco | 606/69 |
| 6,017,343 | A * | 1/2000 | Rogozinski | 606/61 |
| 6,248,106 | B1 | 6/2001 | Ferree | |
| 6,346,000 | B1 * | 2/2002 | Orr | 439/342 |
| 6,379,354 | B1 * | 4/2002 | Rogozinski | 606/61 |
| 6,565,568 | B1 * | 5/2003 | Rogozinski | 606/61 |
| 6,626,909 | B2 * | 9/2003 | Chin | 606/61 |
| 2002/0055741 | A1 | 5/2002 | Schlapfer et al. | |
| 2002/0151896 | A1 | 10/2002 | Ferree | |
| 2003/0163132 | A1 | 8/2003 | Chin | |
| 2004/0006343 | A1 | 1/2004 | Sevrain | |

* cited by examiner

*Primary Examiner*—Eduardo C Robert
*Assistant Examiner*—Jerry Cumberledge
(74) *Attorney, Agent, or Firm*—Stroock & Stroock & Lavan LLP

(57) ABSTRACT

An apparatus for use with bone fasteners comprises a first fixation device having a slot configured to receive a bone fastener, and a second fixation device having another slot configured to receive another bone fastener. The first and second fixation devices are interconnected for rotation relative to each other when the bone fasteners are in the slots. Summarized differently, an apparatus for use with bone fasteners comprises a first fixation device having a first pair of openings defining bone fastener locations, and a second fixation device having a second pair of openings defining bone fastener locations. The first and second fixation devices are interconnected for movement relative to each other such that the bone fastener locations defined by the first and second pairs of openings are located at four corners of a rectangular array.

18 Claims, 3 Drawing Sheets

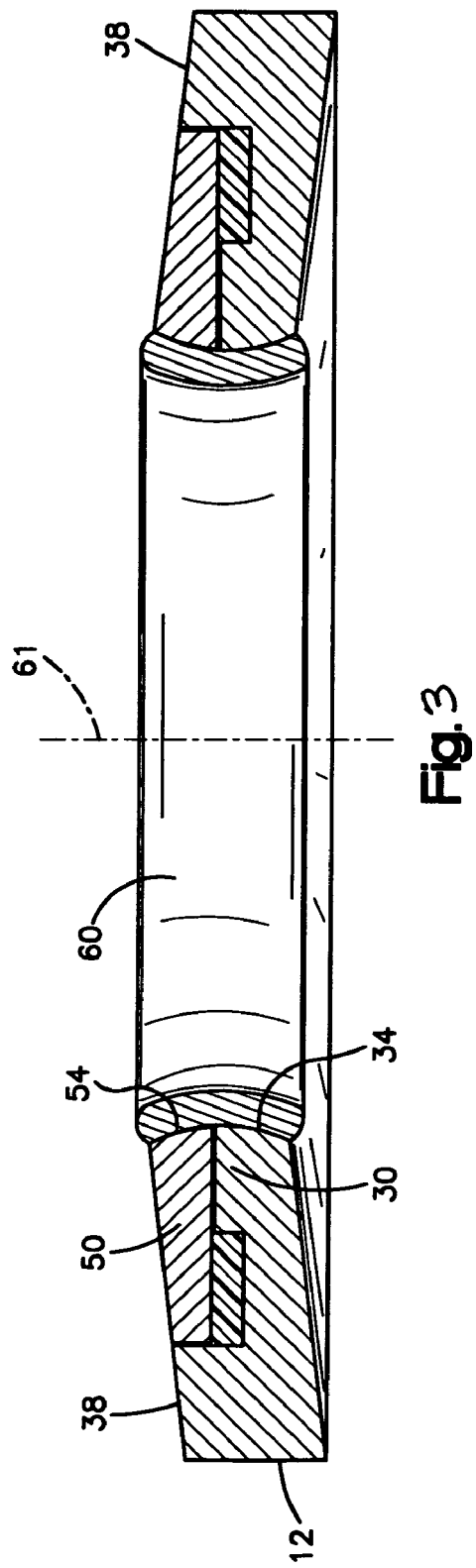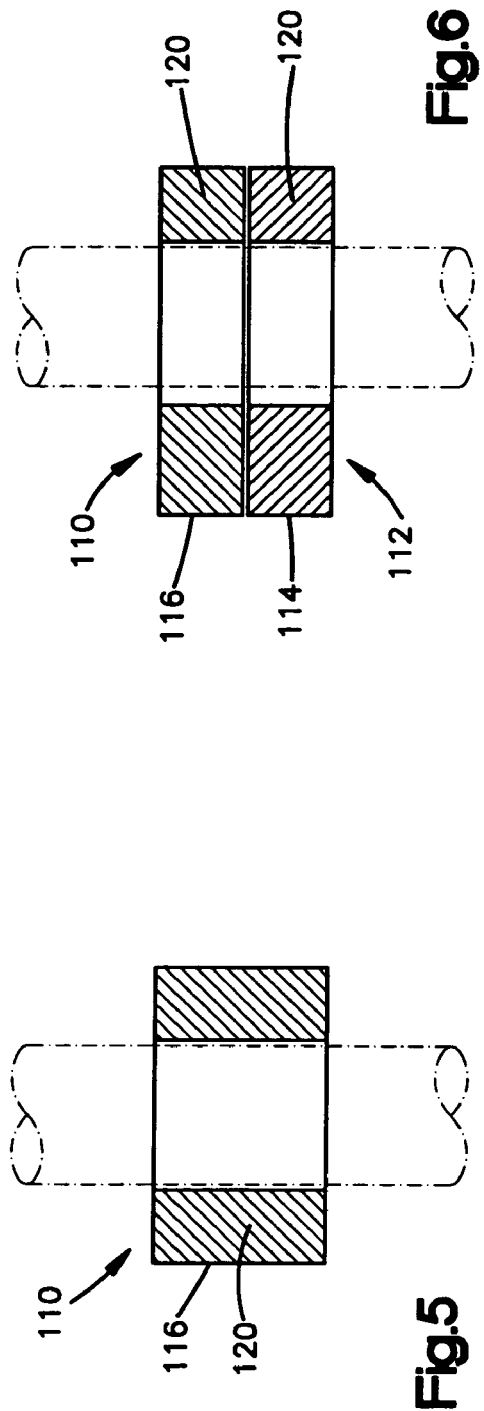

TRANSLATIONAL SCISSOR PLATE FIXATION SYSTEM

FIELD OF THE INVENTION

The present invention is related to a fixation system. More particularly, the invention is related to a fixation system comprising a plurality of rotatably-connected plates each having at least one fixation hole.

BACKGROUND OF THE INVENTION

Orthopedic fixation devices such as plates are frequently coupled to bone with fasteners inserted through plate holes. It is known that securing such fasteners to the bone plate, for example through the use of expansion-head screws, can decrease the incidence of loosening of the fixation assembly post-operatively. It is also known that a bushing may be disposed in each plate hole to receive the fastener to permit polyaxial movement so that the fastener may be angulated at a surgeon-selected angle. However, polyaxial movement of fasteners through set plate hole locations only increases attachment alternatives of the fasteners themselves. The plate holes remain fixed in relation to each other and to the longitudinal axis of the plate.

Typically, a spinal fixation plate is applied to the anterior side of the affected vertebrae to span at least one affected disc space or vertebra (i.e. one in which at least a portion of the disc has been removed and a spinal fusion spacer has been inserted). The plate is fixed to the vertebrae using bone screws and acts to keep the vertebrae generally aligned during the initial period following fixation in which fusion of the spacer to the adjacent vertebrae occurs. The plate also acts to prevent the spacer from being expelled from the disc space during this initial period.

Where a spinal fusion spacer is implanted between a pair of vertebrae to be fused, the spacer rests on the endplates of the vertebrae. The outer circumference of the end plates comprises hard cortical bone and thus provides a the best surface upon which to seat the spacer. The center portion of the endplates comprises a thin cortical bone shell overlying a core of softer cancellous bone. Most, if not all, of the spacer contact surface, however, may be located in this center portion.

Subsequent to placement of the spacer, the surgeon typically compresses the disc space by pressing the adjacent vertebrae together. This compression ensures a good engagement between the spacer the endplates, increasing the chances that fusion will occur. Often in the period immediately following surgery, the spacer will subside slightly either into the under-portion of the endplates or due to graft resorption (in the case of allograft spacers).

Where a rigid fixation plate is used to connect the vertebrae, this subsidence may tend to shift more of the spinal load to the plate than is desirable. Such load shifting can also occur due to inaccuracies in installing the plate to the vertebrae. In extreme circumstances, this load shifting can result in non-fusion of the spacer to the vertebra, since firm compression between the spacer and the vertebrae is one factor contributing to successful fusion.

Accordingly, there exists a need for a fixation system which provides the desired support to the vertebrae to be fused, and which allows limited translation of the vertebrae with respect to at least a portion of the plate, thereby limiting the undesirable effects of load shielding by the plate due to graft subsidence caused by settling or normal forces experienced in the spinal column. Promoting fusion of the adjacent vertebrae is thus accomplished.

The inventive translation plates compensate for this subsidence by providing the aforementioned benefits of a rigid fixation plate (general vertebral alignment, prevention of spacer expulsion), while allowing at least one vertebra to move with respect to the plate to compensate for the post-surgical subsidence. This compensation ensures that the majority of the spinal column load is borne by the spacer rather than the plate.

SUMMARY OF THE INVENTION

An apparatus for use with bone fasteners comprises a first fixation device having a slot configured to receive a bone fastener, and a second fixation device having another slot configured to receive another bone fastener. The first and second fixation devices are interconnected for rotation relative to each other when the bone fasteners are in the slots.

Summarized differently, an apparatus for use with bone fasteners comprises a first fixation device having a first pair of openings defining bone fastener locations, and a second fixation device having a second pair of openings defining bone fastener locations. The first and second fixation devices are interconnected for movement relative to each other such that the bone fastener locations defined by the first and second pairs of openings are located at four corners of a rectangular array. The bone fastener locations at opposite ends of the rectangular array are movable relatively toward each other lengthwise of the array while remaining uniformly spaced apart from each other across the array.

A fixation assembly is described comprising a first fixation device having a first opening configured to receive a first bone fastener, and a second opening configured to receive a second bone fastener; and a second fixation device having a third opening configured to receive a third bone fastener, and a fourth opening configured to receive a fourth bone fastener; wherein the first and third openings form a first pair of openings and the second and fourth openings form a second pair of openings; the fixation devices arranged so that when first and third bone fasteners are at least partially inserted through the first pair of openings and into a first bone segment, and second and fourth bone fasteners are at least partially inserted through the second pair of openings and into a second bone segment, the first and second bone fixation devices are able to rotate relative to each other.

The first fixation device may have a first substantially circular portion having a first midpoint, the second fixation device may have a second substantially circular portion having a second midpoint; and wherein the first and second midpoints may generally align when the first and second fixation devices are engaged. The first midpoint and the first and second openings may be generally collinear, and the second midpoint and the third and fourth openings may be generally collinear.

The first fixation device may further comprise first and second extensions projecting radially from the first midpoint, and the second fixation device may further comprise third and fourth extensions projecting radially from the second midpoint. The first opening may be located at the first extension, the second opening may be located at the second extension, the third opening may be located at the third extension, and the fourth opening may be located at the fourth extension.

At least one bone fastener may be allowed to translate within an opening in situ. The first and second bone segments may be adjacent vertebrae. The movement of either the first or second bone segments relative to one another may cause the attached bone fasteners to translate within their respective openings. The movement of either the first or second bone segments relative to one another may cause the first and second fixation devices to rotate relative to each other.

The first fixation device may have an upper and lower surface, and the second fixation device may have an upper and lower surface, and wherein the lower surface of the first fixation device may be configured to slidably engage the upper surface of the second fixation device. The upper surface of the second fixation device may further comprise a groove, wherein at least a portion of the lower surface of the first fixation device may be configured to engage at least a portion of the groove.

The assembly may further comprise a hub for connecting the first and second fixation devices. At least one opening may be a slot. The assembly may further comprise a third fixation device and a fourth fixation device.

A fixation assembly is also described comprising a first and second pair of openings arranged in a generally rectangular array, wherein each opening is configured to receive a bone fastener; a first distance extending between the first pair of openings, and a second distance extending between the second pair of openings, wherein the translation of bone fasteners within the openings alters at least one of the first and second distances.

The first and second pairs of openings may be slots. The slots may be centered on axes that extend between diagonally opposite corners of the rectangular array.

A fixation assembly is further described, comprising a first fixation device having a first pair of openings defining bone fastener locations; and a second fixation device having a second pair of openings defining bone fastener locations; the first and second fixation devices being interconnected for movement relative to each other such that the bone fastener locations defined by the first and second pairs of openings are located at four corners of a rectangular array, and the bone fastener locations at opposite ends of the rectangular array are movable relatively toward each other lengthwise of rectangular array while remaining uniformly spaced apart from each other across the rectangular array.

The first and second bone fixation devices may be interconnected for rotation relative to each other. The first and second pairs of openings may be slots.

BRIEF DESCRIPTION OF THE DRAWINGS

Preferred features of the present invention are disclosed in the accompanying drawings, wherein similar reference characters denote similar elements throughout the several views, and wherein:

FIG. 3 is an enlarged cross-sectional view taken on line A-A of FIG. 1.

FIG. 5 is a cross-sectional view taken on line B-B of FIG. 4.

FIG. 6 is a cross-sectional view taken on line C-C of FIG. 4.

DETAILED DESCRIPTION OF THE INVENTION

The plates described herein may be used in spinal fusion procedures in which a damaged or diseased disc (or part of a disc) is removed from between a pair of vertebrae and a spinal fusion spacer is placed between the vertebrae. The plates may be applied to an anterior portion of the affected vertebrae to span the affected disc space, and may be fixed to the vertebrae using bone screws. The plate may function to maintain the vertebrae aligned during the initial period following fixation in which fusion of the spacer to the adjacent vertebrae occurs. The plate may also function to share some of the axial spinal load applied to the fusion spacer to prevent extreme subsidence of the spacer into the vertebral body, such as where the patient has poor bone quality. The plates may also act to prevent the spacer from being expelled from the disc space during the initial post-operative period.

The plates may be used for single-level (i.e. one-disc) or multiple-level (i.e. multiple disc) fusion procedures. Some embodiments may be used for corpectomy procedures, in which at least a portion of a vertebral body is removed. Single level plates generally may have two pairs of fastener holes, while the multi-level plates generally may have three or more pairs of holes.

Figure 1:
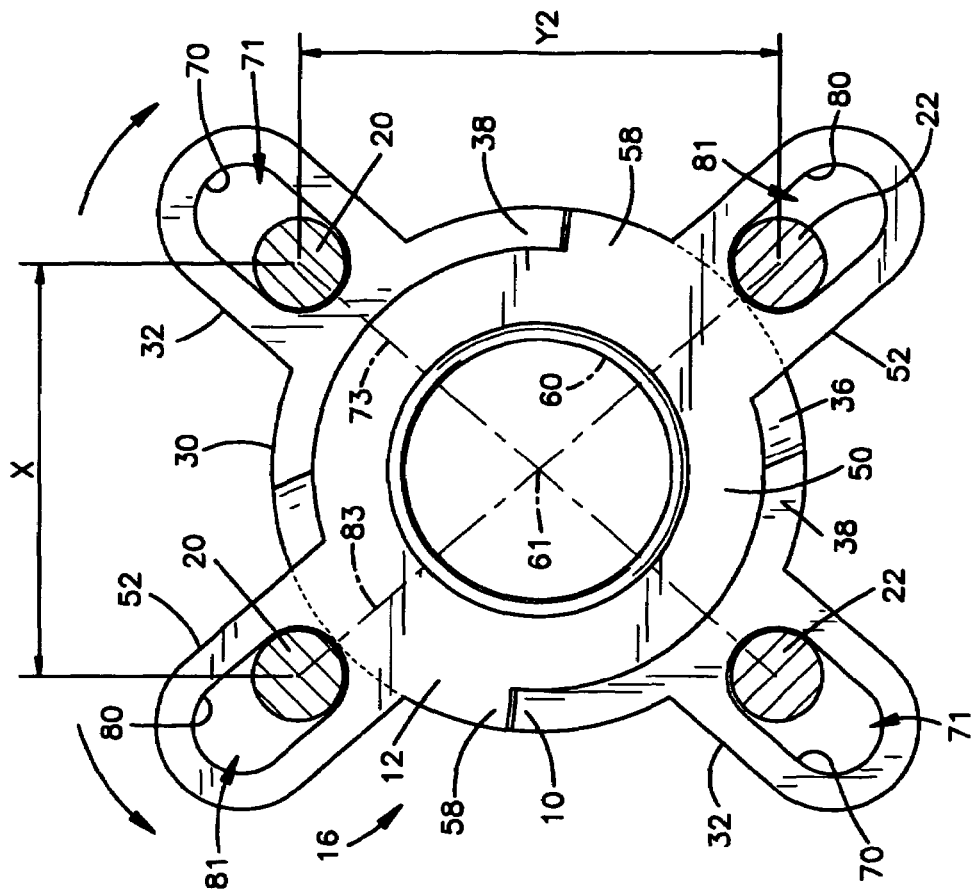
FIG. 1 is a top view of an embodiment of a one-level bone fixation assembly in an expanded position.
Figure 2:
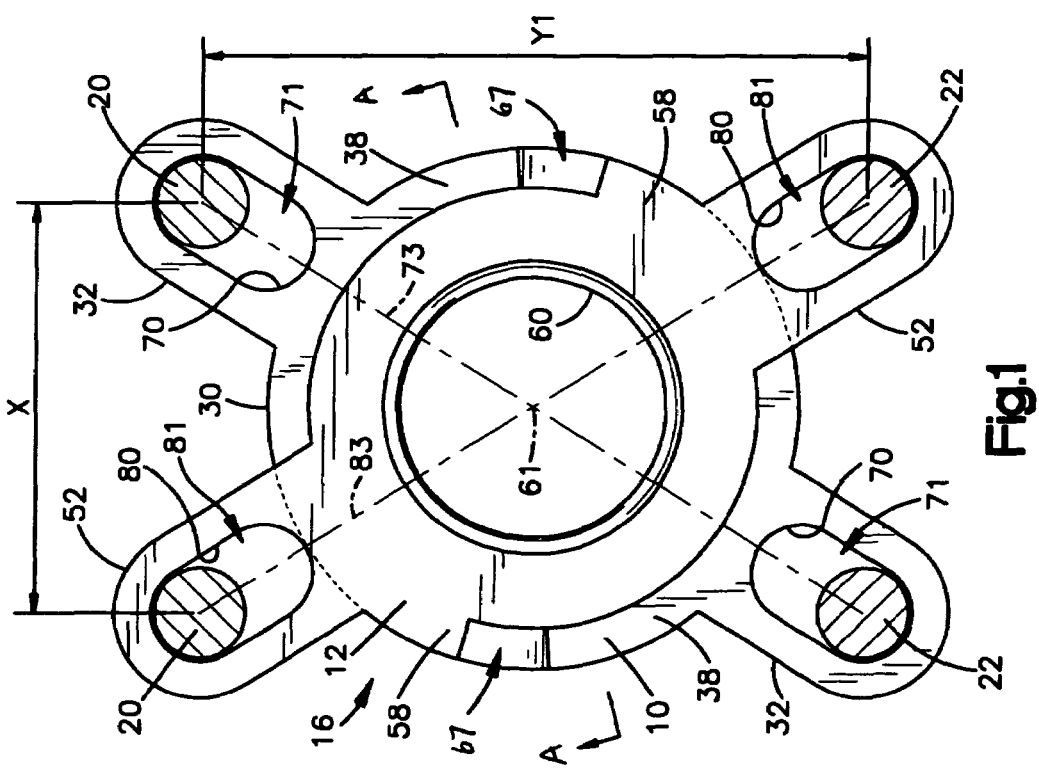
FIG. 2 is a top view of the assembly of FIG. 1, in a compressed position.

FIGS. 1-3 show an embodiment of a one-level bone fixation assembly. This embodiment includes first and second bone fixation plates 10 and 12. The bone fixation plates 10 and 12 together define a bone fixation assembly 16 which, in this particular example, is a spinal fixation assembly.

A first pair of fasteners 20 fasten the fixation assembly 16 to a first vertebra. A second pair of fasteners 22 fasten the fixation assembly 16 to a second vertebra adjacent to the first vertebra. The fixation plates 10 and 12 are interconnected for movement relative to each other such that the two pairs of fasteners 20 and 22 can move toward each other vertically while the fasteners 20 or 22 in each pair remain uniformly spaced apart from each other horizontally. This enables the fixation assembly 16 to shift as needed when compression of the spinal column causes the two fastened vertebra to move toward each other.

In the embodiment of FIG. 1, the first bone fixation plate 10 is a plate with a circular central portion 30. A pair of opposite end portions 32 of the plate 10 may project radially outward from the central portion 30 at diametrically opposite locations. The central portion 30 may be shaped as a ring with an annular inner edge surface 34 (see FIG. 3). A pair of shoulders 38 may be located at the periphery of the central portion 30. Each shoulder 38 may project axially upward, as shown in FIG. 3, and may extend in an arc past the location of a respective one of the outer end portions 32, as shown in FIG. 1.

The embodiment shown in FIG. 1 also has a second bone fixation plate 12 with a ring-shaped central portion 50, which may have a pair of opposite end portions 52 projecting radially outward from the central portion 50 at diametrically opposite locations. The ring-shaped central portion 50 of the second plate 12 may be received concentrically over the ring-shaped central portion 30 of the first plate 10, and may fit closely between the shoulders 38 on the first plate 10.

Second plate 12 may similarly have a pair of shoulders 58. As shown in FIG. 3, an annular inner edge surface 54 of the second plate 12 may be located adjacent to the annular inner edge surface 34 of the first plate 10. A ring-shaped hub 60 may be crimped against the annular inner edge surfaces 34 and 54. The hub 60 may hold the two plates 10 and 12 together, and may support them for sliding movement relative to each other rotationally about a common central axis 61. The range of such movement may be defined by the circumferential length of the spaces 67 between the shoulders 38 and 58 when the two plates 10 and 12 are in the positions shown in FIG. 1. The plates 10 and 12 are thus rotatable from the initial, expanded positions of FIG. 1 toward the rotated, compressed positions of FIG. 2. An elastomeric friction ring 64, shown in FIG. 3, may be interposed between the plates 10 and 12 to prevent the plates 10 and 12 from rattling or rotating loosely.

The opposite end portions 32 of the first plate 10 may be similarly dimensioned, shaped, and/or sized. Each end portion 32 may have an inner edge surface 70 defining a respective slot 71. The slots 71 may be centered on a line 73 extending diametrically across the circular central portion 30 of the first plate 10, and may be elongated radially. The opposite end portions 52 of the second plate 12 likewise may have inner edge surfaces 80 defining radially elongated slots 81 that may be centered on a diametrically extending line 83, and may generally have all of the characteristics of the opposite end portions 32 of the first plate 10. Slots 71 may also be fitted with captive clips (not shown) to allow fasteners 20 and 22 to move within the slots 71 and further prevent fastener 20 and 22 back-out, the details, materials, and methods of which are described in U.S. patent application Ser. No. 10/653,164 entitled "Bone Plate with Captive Clips", by Duong, et al., filed Sep. 3, 2003, the entire disclosure of which application is expressly incorporated by reference herein.

The fixation assembly 16 may be shiftable from the initial, expanded condition of FIG. 1 to the shifted, compressed condition of FIG. 2 upon rotation of the first and second plates 10 and 12 relative to each other about the axis 61. When the spinal fixation assembly 16 is in the initial, expanded condition of FIG. 1, the slots 71 and 81 in the two plates 10 and 12 may define the locations at which the first and second pair of fasteners 20 and 22 are to be implanted into the first and second vertebra. Specifically, the first pair of fasteners 20 may be implanted into the first vertebra at the radially outer ends of the slots 71 and 81 in the upper end portions 32 and 52 of the plates 10 and 12. The second pair of fasteners 22 may be implanted into the second vertebra at the radially outer ends of the slots 71 and 81 in the lower end portions 32 and 52 of the plates 10 and 12. The first and second pairs of fasteners 20 and 22 may then be located at the four corners of a generally rectangular array in which the diametrically extending lines 73 and 83 may extend as diagonal axes between diagonally opposite corners of the array.

Compression of the spine may cause the first and second vertebra to move toward each other. This may cause the first pair of fasteners 20 at the first vertebra to move vertically downward relative to the second pair of fasteners 22 at the second vertebra. The vertebral spacing between the first and second pair of fasteners 20 and 22 at the opposite ends of the generally rectangular array may thus be reduced from the expanded distance "Y1" of FIG. 1 either partially or fully to the compressed distance "Y2" of FIG. 2. However, such shifting of the vertebra does not cause the first and second pair of fasteners 20 or 22 to move horizontally within the vertebra to which they are fastened. Therefore, the horizontal spacing "X" across the generally rectangular array of bone screws 20 and the 22 remains constant as the first and second vertebrae move toward each other. When the first pair of fasteners 20 move toward the second pair of fasteners 22 in this manner, their respective locations may therefore shift in the slots 71 and 81 such that each fasteners 20 and 22 moves radially inward of the respective slot 71 or 81. The fasteners 20 and 22 may then slide against the inner edge surfaces 70 and 80 in the slots 71 and 81 so as to move the plates 10 and 12 rotationally about the axis 61 from the expanded positions of FIG. 1 toward the compressed positions of FIG. 2. The fixation assembly 16 is thus shiftable to accommodate movement of the fastened vertebra while remaining fastened to those vertebra to provide alignment support for the spine.

Figure 4:
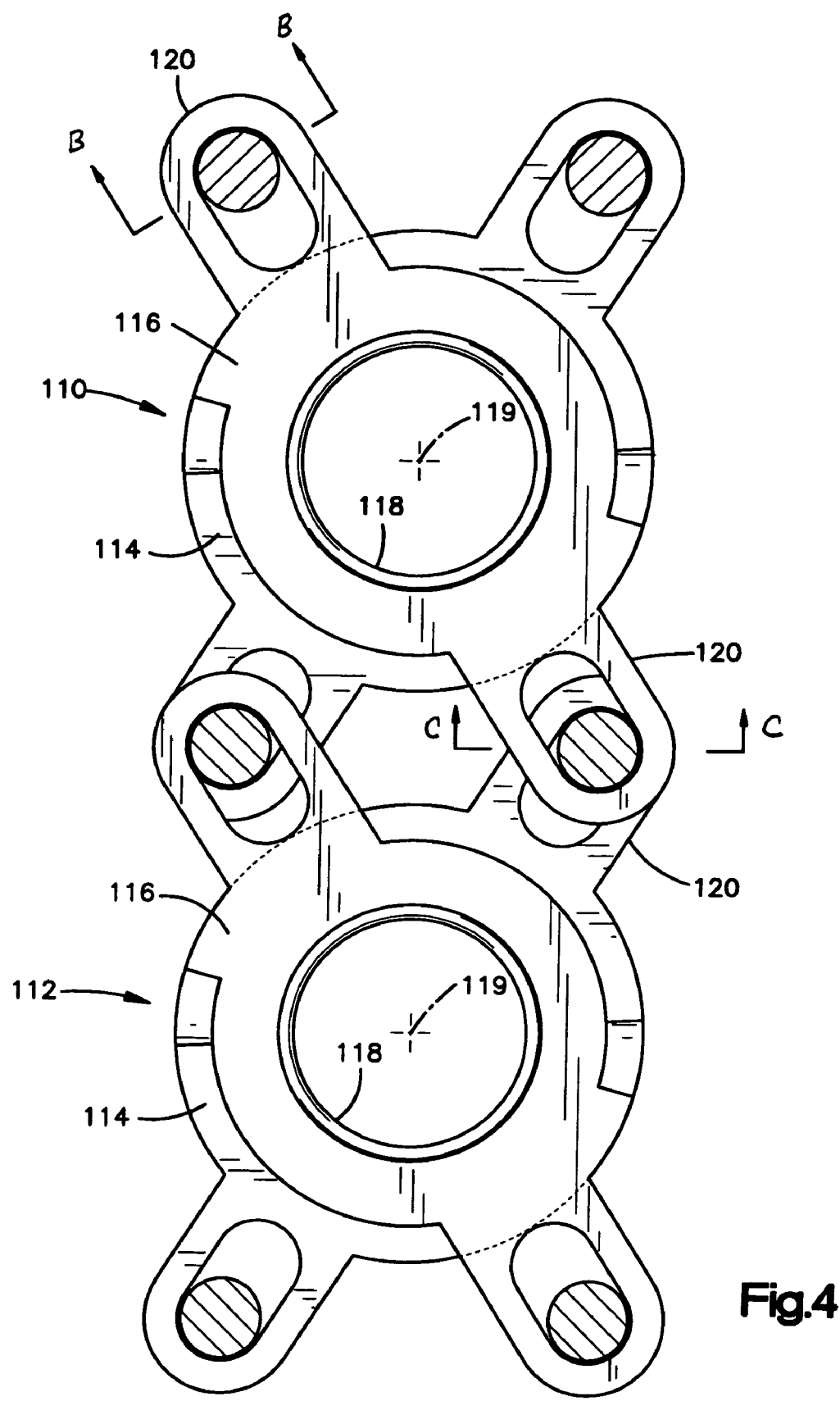
FIG. 4 is a top view of an embodiment of a two-level bone fixation assembly in an expanded position.

FIGS. 4-6 shows an embodiment of a two-level fixation assembly. This embodiment includes first and second shiftable bone fixation assemblies 110 and 112 that are together configured to be fastened to the spinal column in a connected series extending along the length of the spinal column. Generally, the fixation assemblies 110 and 112 and their components shown in FIGS. 4-6 may have some or all of the characteristics of the fixation assembly 16 shown in FIGS. 1-3.

Each fixation assembly 110 and 112 of FIG. 4 is substantially the same as the bone fixation assembly 16 of FIGS. 1-3, and thus includes first and second fixation plates 114 and 116 that may be interconnected by a hub 118 for rotation relative to each other about a common central axis 119 as described above with reference to the fixation assembly 16. However, the bone fixation assemblies 110 and 112 differ in that an end portion 120 of a plate 114 or 116 has a full thickness at a free end of the connected series, as shown in FIG. 5, or a reduced thickness where adjacent end portions 120 overlap in the connected series, as shown in FIG. 6.

Generally, fixation plates 10, 12, 114, 116 may be of any suitable size, shape, and dimension, depending at least in part on the size of the vertebra the plates will be attached to, and the size of the intervertebral space to be spanned. Fixation plates 10, 12, 114, 116 may be substantially flat, to reduce the overall profile of the fixation assembly 16, 110, 112.

Each of the fasteners and fixation plates disclosed herein may be formed of a titanium alloy such as titanium-aluminum-niobium, which may be anodized. One material for use with each of the plates and screws described herein is Ti-6AI-7Nb, with a density of about 4.52 gm/cc, a modulus of elasticity of about 105 GPa, an ultimate tensile strength of about 900 MPa, and a yield strength of about 800 MPa. Surfaces of the fasteners may also be burr free, with all sharp edges broken to a maximum of 0.1 mm.

It should be noted that the aforementioned descriptions and illustrations have been provided as examples of the configurations of translation plates that may be designed and assembled using the principles of the invention. These examples will be understood to one of ordinary skill in the art as being non-limiting in that a fixation assembly employing one or more of the disclosed features may be produced as desired or required for a particular patient's need. Thus, the features disclosed are "modular" in nature.

This written description sets forth the best mode of the claimed invention, and describes the claimed invention to enable a person of ordinary skill in the art to make and use it, by presenting examples of the elements recited in the claims. The patentable scope of the invention is defined by the claims themselves, and may include other examples that occur to those skilled in the art. Such other examples, which may be available either before or after the application filing date, are intended to be within the scope of the claims if they have structural elements that do not differ from the literal language of the claims, or if they include equivalent structural elements with insubstantial differences from the literal language of the claims.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

The invention claimed is:

1. A fixation assembly comprising:
a first fixation device comprising first and second extensions projecting radially from a first central portion, the first extension having a first elongated opening configured to receive a first bone fastener, a second elongated the second extension having opening configured to receive a second bone fastener, the first fixation device further comprising a first central portion located in-between the first and second elongated openings wherein the first central portion has a first annular inner edge surface and a first shoulder located in-between the first annular inner edge surface and the first elongated opening and a second shoulder located in-between the first annular inner edge surface and the second elongated opening; and a second fixation device comprising third and fourth extensions projecting radially from a second central portion, the third extension having a third elongated opening configured to receive a third bone fastener, the fourth extension having a fourth elongated opening configured to receive a fourth bone fastener, the second fixation device further comprising a second central portion located in-between the third and fourth elongated openings wherein the second central portion has a second annular inner edge surface and a third shoulder located in-between the second annular inner edge surface and the third elongated opening and a fourth shoulder located in-between the second annular inner edge surface and the fourth elongated opening;

wherein the first and third elongated openings form a first pair of openings and the second and fourth elongated openings form a second pair of openings, the first pair of openings being separated from the second pair of openings by a distance A and the circumferential distance between the first shoulder and the third shoulder is equal to the circumferential distance between the second shoulder and the fourth shoulder;

wherein at least a portion of the first central portion overlaps at least a portion of the second central portion and a central hub is placed between the first annular inner edge surface and the second annular inner edge surface to connect the first fixation device and second fixation device;

the fixation devices arranged so that when first and third bone fasteners are at least partially inserted through the first pair of openings and into a first bone segment, and second and fourth bone fasteners are at least partially inserted through the second pair of openings and into a second bone segment, the first and second fixation devices are permitted to rotate relative to each other in a range not to exceed the circumferential distance between the first shoulder and the third shoulder so that the distance A between the first and second pairs of openings is permitted to change in situ.

2. The assembly of claim 1, wherein the first central portion has a first substantially circular portion having a first midpoint, the second central portion has a second substantially circular portion having a second midpoint; and wherein the first and second midpoints generally align when the first and second fixation devices are engaged.

3. The assembly of claim 2, wherein the first midpoint and the first and second openings are generally collinear, and the second midpoint and the third and fourth openings are generally collinear.

4. The assembly of claim 1, wherein at least one bone fastener is allowed to translate within an opening in situ.

5. The assembly of claim 1, wherein the first and second bone segments are adjacent vertebrae.

6. The assembly of claim 1, wherein the movement of either the first or second bone segments relative to one another causes the inserted bone fasteners to translate within their respective openings.

7. The assembly of claim 1, wherein the movement of either the first or second bone segments relative to one another causes the first and second fixation devices to rotate relative to each other.

8. The assembly of claim 1, wherein the first fixation device has an upper and lower surface, and the second fixation device has an upper and lower surface, and wherein the lower surface of the first fixation device is configured to slidably engage the upper surface of the second fixation device.

9. The assembly of claim 8, the upper surface of the second fixation device further comprising a groove, wherein at least a portion of the lower surface of the first fixation device is configured to engage at least a portion of the groove.

10. The assembly of claim 1, further comprising a third fixation device and a fourth fixation device.

11. The assembly of claim 1, wherein the first and third elongated openings form a first pair of adjacent openings and the second and fourth elongated openings form a second pair of adjacent openings.

12. A fixation assembly comprising:
a first fixation device having:
a first end that projects radially from a first central portion with a first hole for receiving a first bone fastener for engaging the first vertebra;
a second end that projects radially from the first central portion with a second hole for receiving a second bone fastener for engaging the second vertebra, at least one of the first and second holes being an elongated slot; and
the first central portion having a first annular inner surface and a first shoulder extending between the first annular inner surface and the first end and a second shoulder extending between the first annular inner surface and the second end;
a second fixation device having:
a first end that projects radially from a second central portion with a third hole for receiving a third bone fastener for engaging the first vertebra;
a second end that projects radially from the second central portion with a fourth hole for receiving a fourth bone fastener for engaging the second vertebra, at least one of the third and fourth holes being an elongated slot; and
with second central portion having a second annular inner surface and a third shoulder extending between the second annular inner surface and the first end and a fourth shoulder extending between the second annular inner surface and the second end;
wherein at least a portion of the first central portion overlaps at least a portion of the second central portion and a central hub is placed between the first annular inner edge surface and the second annular inner edge surface to connect the first fixation device and second fixation device and the circumferential distance between the first shoulder and the third shoulder is equal to the circumferential distance between the second shoulder and the fourth shoulder; and wherein when the fixation assembly is implanted within a patient, at least one of the first and third bone fasteners or the second and fourth bone fasteners is permitted to be separated by a distance X; at least one of the first and fourth bone fasteners or the second and third bone fasteners is permitted to be separated by a distance Y; and the first fixation device is permitted to rotate with respect to the second fixation device in a range not to exceed the circumferential distance between the first shoulder and the third shoulder such that the distance X remains substantially constant while the distance Y is permitted to vary.

13. A fixation assembly comprising:

a first fixation device having:
- a first end that projects radially from a first central portion having with a first hole for receiving a first bone fastener for engaging a first vertebra;
- a second end that projects radially from the first central portion with a second hole for receiving a second bone fastener for engaging a second vertebra, at least one of the first and second holes being an elongated slot; and
- with first central portion a first annular inner surface and a first shoulder extending between the first annular inner surface and the first end and a second shoulder extending between the first annular inner surface and the second end;

a second fixation device having:
- a first end that projects radially from a second central portion having a third hole for receiving a third bone fastener for engaging the first vertebra;
- a second end that projects radially from the second central portion having a fourth hole for receiving a fourth bone fastener for engaging the second vertebra, at least one of the third and fourth holes being an elongated slot; and
- with second central portion having a second annular inner surface and a third shoulder extending between the second annular inner surface and the first end and a fourth shoulder extending between the second annular inner surface and the second end;

wherein at least a portion of the first central portion overlaps at least a portion of the second central portion and a central hub is placed between the first annular inner edge surface and the second annular inner edge surface to connect the first fixation device and second fixation device; and wherein when the fixation assembly is implanted within a patient, the first fixation device is permitted to move with respect to the second fixation device between the first and third shoulders and second and fourth shoulders respectively to permit in situ compression of the first vertebra with respect to the second vertebra.

14. The fixation assembly of claim 13, wherein the first fixation device is permitted to rotate with respect to the second fixation device.

15. The fixation assembly of claim 13, wherein the first hole formed in the first fixation device is sized and configured to receive a first bone fastener and the third hole formed in the second fixation device is sized and configured to receive a third bone fastener, the first and third bone fasteners being separated by a distance X, the second hole formed in the first fixation device and the fourth hole formed in the second fixation device are also sized and configured to receive the second and fourth bone fasteners, respectively, the second and fourth bone fasteners being separated by the distance X, the first bone fastener formed in the first fixation device and the fourth bone fastener formed in the second fixation device are separated by a distance Y, the second bone fastener formed in the first fixation device and the third bone fastener formed in the second fixation device are also separated by the distance Y, and, when the fixation assembly is implanted within a patient, the first fixation device is permitted to move with respect to the second fixation device such that the distance X remains substantially constant while the distance Y is permitted to vary.

16. The fixation assembly of claim 13, wherein the first and second holes formed in the first fixation device and the third and fourth holes formed in the second fixation device form a rectangular array, the rectangular array having a width X and a height Y so that when the fixation assembly is implanted within a patient, the first fixation device is permitted to move with respect to the second fixation device such that the distance X remains substantially constant while the distance Y is permitted to vary.

17. The fixation assembly of claim 13, wherein the first fixation device has an upper surface and a lower surface, and the second fixation device has an upper surface and a lower surface, the lower surface of the first fixation device is configured to slidably engage the upper surface of the second fixation device.

18. The fixation assembly of claim 17, wherein the upper surface of the second fixation device further comprising a groove, wherein at least a portion of the lower surface of the first fixation device is configured to engage at least a portion of the groove.

* * * * *